(12) United States Patent
Gilding et al.

(10) Patent No.: US 12,090,030 B2
(45) Date of Patent: Sep. 17, 2024

(54) WOUND EXUDATE MANAGEMENT SYSTEMS

(71) Applicant: CONVATEC LIMITED, Deeside (GB)

(72) Inventors: Duncan C. Gilding, Nantwich (GB); Andrew Peers, Buckley (GB); Shauna V. Powell, Runcorn (GB)

(73) Assignee: CONVATEC LIMITED, Deeside (GB)

(*) Notice: Subject to any disclaimer, the term of this patent is extended or adjusted under 35 U.S.C. 154(b) by 0 days.

(21) Appl. No.: 17/065,876

(22) Filed: Oct. 8, 2020

(65) Prior Publication Data
US 2021/0100691 A1     Apr. 8, 2021

Related U.S. Application Data

(60) Provisional application No. 62/912,372, filed on Oct. 8, 2019.

(51) Int. Cl.
*A61F 13/05*     (2024.01)
*A61F 13/00*     (2024.01)
(Continued)

(52) U.S. Cl.
CPC ........ *A61F 13/05* (2024.01); *A61F 13/00055* (2013.01); *A61F 13/0206* (2013.01);
(Continued)

(58) Field of Classification Search
CPC ............ A61F 13/0206; A61F 13/00055; A61F 13/00068; A61M 1/90; A61M 2205/75;
(Continued)

(56) References Cited

U.S. PATENT DOCUMENTS 10,779,993 B2    9/2020    Bishop et al.
11,819,386 B2    11/2023   Brandolini et al.
(Continued)

FOREIGN PATENT DOCUMENTS

CN          1545991 A        6/2006
CN      109464727 A    *    3/2019    ............ A61M 5/178
(Continued)

OTHER PUBLICATIONS

Zhao W, Filtering Exudate Syringe (Year: 2018).*
(Continued)

*Primary Examiner* — Sarah Al Hashimi
*Assistant Examiner* — Nhu Q. Tran
(74) *Attorney, Agent, or Firm* — Taft Stettinius & Hollister LLP; Ryan O. White; Derek B. Lavender

(57) ABSTRACT

A wound dressing according to certain embodiments includes an adhesive layer for adhering the wound dressing adjacent to a wound, a wound contact layer for contacting the wound, a backing layer comprising a port, a tube having a first end connected with the port and an opposite second end, a first fitting connected to the second end of the tube, the first fitting configured for connection with a second fitting of the negative pressure wound therapy system to apply a negative pressure via the port, and a filter disposed within the first fitting. In certain embodiments, the filter is formed of polyethersulfone (PESU) and has an average pore size of at least 2 microns.

15 Claims, 4 Drawing Sheets

(51) Int. Cl.
*A61F 13/0206* (2024.01)
*A61M 1/00* (2006.01)
*A61M 39/24* (2006.01)

(52) U.S. Cl.
CPC .............. *A61M 1/784* (2021.05); *A61M 1/79* (2021.05); *A61M 1/86* (2021.05); *A61M 1/912* (2021.05); *A61M 1/915* (2021.05); *A61M 39/24* (2013.01); *A61M 1/92* (2021.05); *A61M 1/985* (2021.05); *A61M 2205/75* (2013.01)

(58) Field of Classification Search
CPC .......... A61M 1/784; A61M 1/79; A61M 1/86; A61M 2039/1072; A61M 39/10
See application file for complete search history.

(56) References Cited

U.S. PATENT DOCUMENTS

| | | | |
|---|---|---|---|
| 2003/0236500 A1 | 12/2003 | Scheu | |
| 2004/0237785 A1* | 12/2004 | Neri | B01D 19/0031 96/7 |
| 2005/0132826 A1* | 6/2005 | Teugels | A61M 1/3639 210/93 |
| 2012/0111807 A1* | 5/2012 | Hillyer | A61M 1/0281 210/806 |
| 2013/0011296 A1* | 1/2013 | Holm | C08J 3/28 422/22 |
| 2013/0338588 A1* | 12/2013 | Grimm | A61M 39/10 604/126 |
| 2014/0005612 A1* | 1/2014 | Guala | A61M 5/16804 604/247 |
| 2014/0074053 A1 | 3/2014 | Locke et al. | |
| 2016/0339226 A1 | 11/2016 | Sealfon | |
| 2018/0168437 A1* | 6/2018 | Schreiner | A61B 1/00128 |
| 2018/0200412 A1 | 7/2018 | Dang et al. | |
| 2018/0345001 A1* | 12/2018 | Heaton | A61M 1/86 |
| 2019/0015258 A1* | 1/2019 | Gowans | A61F 13/00068 |
| 2020/0330662 A1* | 10/2020 | Hartwell | A61M 1/74 |

FOREIGN PATENT DOCUMENTS

| | | | |
|---|---|---|---|
| CN | 106061547 A | 5/2020 | |
| CN | 109414351 A | 6/2022 | |
| EP | 3520830 B1 | 10/2023 | |
| EP | 3595734 B1 | 11/2023 | |
| JP | 2013529942 A | 7/2013 | |
| JP | 2014506164 A | 3/2014 | |
| WO | 2011135285 A1 | 11/2011 | |
| WO | 2012087376 A1 | 6/2012 | |
| WO | 2017087163 A1 | 5/2017 | |
| WO | WO-2017196888 A1 * | 11/2017 | .............. A61M 1/73 |

OTHER PUBLICATIONS

International Search Report; European Patent Office; International Application No. PCT/IB2020/000837; Feb. 3, 2021; 4 pages.

Written Opinion of the International Searching Authority; European Patent Office; International Application No. PCT/ B2020/000837; Feb. 3, 2021; 8 pages.

* cited by examiner

WOUND EXUDATE MANAGEMENT SYSTEMS

CROSS-REFERENCE TO RELATED APPLICATIONS

The present application claims the benefit of U.S. Provisional Patent Application No. 62/912,372, filed 8 Oct. 2019, the contents of which are incorporated by reference in their entirety.

TECHNICAL FIELD

The present disclosure generally relates to wound exudate management systems, and more particularly but not exclusively relates to inline filters for such wound exudate management systems.

BACKGROUND

Wound healing is composed of four phases: hemostasis, inflammation, proliferation, and maturation. Managing exudate during the hemostasis and proliferation phases of wound healing is vital to prevent maceration, recurring infection, and other adverse effects on the patients. Wound dressings that exert negative pressure at the site of wound absorb excess excaudate and promote healing. Exerting and maintaining negative pressure of wound dressings is ideal for treating and managing various types of chronic or acute dermal wounds stemmed from infection, ulcers, burns, abrasions, incisions, lacerations, punctures, avulsions, and amputations.

Wound exudate management systems comprising a negative pressure generating system (such as a pump or a vacuum source) can be used in conjunction with wound dressings to achieve negative pressure at the site of a wound without the need of a canister. However, exudate from the wound can exceed the absorbing capacity of the wound dressing and subsequently enter the wound exudate management system, which may damage the components of the system, including the pump unit. Additionally, excess exudate can create blockage in the wound exudate management system, disrupting the maintenance of the negative pressure. For these reasons and others, there remains a need for further developments in this technological field.

SUMMARY

Disclosed herein are inline filters and methods of using the inline filters. Described herein are inline filters as part of the wound exudate management systems and methods of using the inline filters as part of the wound exudate management systems.

Disclosed herein are methods, systems and process for inline filters, the inline filters comprising an inlet opening having a first connector; an outlet opening having a second connector; and a cartridge flanked by the inlet and outlet openings, the cartridge comprising a cavity, a one-way check valve, and at least one filter membrane. In some embodiments, the one-way check valve and the at least one filter membrane are housed inside the cavity and perpendicular to the inlet and outlet openings. In other embodiments, the at least one filter membrane is positioned between the one-way check valve and the outlet opening. In still other embodiments, the at least one filter membrane is positioned between the inlet opening and the one-way check valve.

In certain embodiments, the filter membrane comprises hydrophilic material. In certain embodiments, the hydrophilic material comprises silver, aluminum, cellulose acetate, ceramic, glass fiber, mixed cellulose ester (MCE), nylon, polyacrylonitrile (PAN), hydrophilic polycarbonate (PCTE), hydrophilic polytetrafluoroethylene (PTFE), hydrophilic polyvinylidene difluoride (PVDF), nitrocellulose, or hydrophilic glass fiber. In some instances, the filter membrane comprises hydrophobic material. In certain instances, the hydrophobic material comprises polyether ether ketone (PEEK), hydrophobic polycarbonate (PCTE), polyethersulfone (PESU), polyester (PETE), polypropylene, hydrophobic polytetrafluoroethylene (PTFE), hydrophobic polyvinylidene difluoride (PVDF), or hydrophobic glass fiber. In certain instances, the filter membrane comprises a pore size of at least 0.2 microns.

Also disclosed herein are methods and processes for wound exudate management system, comprising a pump for generating negative pressure; a wound dressing for covering and protecting a wound; an inline filter; and a first pressure tube having an interior lumen, a second pressure tube having an interior lumen, and a flexible connector, wherein the first pressure tube is disposed between the pump and the inline filter, the second pressure tube is disposed between the inline filter and the flexible connector, and the flexible connector is disposed between the second pressure tube and the wound dressing such that the pump and the wound dressing are in fluid communication via the interior lumen. In some instances, the wound dressing comprises an adhesive layer for adhering the wound dressing adjacent to the wound. In certain instances, the wound dressing comprises a wound contact layer for contacting the wound, a pressure dispersion layer, a plurality of layers of absorbent material disposed between the wound contact layer and the pressure dispersion layer; and a backing layer having a first surface and a second surface, the first surface of the backing layer being adjacent, and in contact with, the pressure dispersion layer and the adhesive layer. In certain instances, the wound dressing comprises a thermoplastic spun lace layer connected to the pressure dispersion layer, and a nonwoven spun lace layer connected to the wound contact layer, wherein an envelope structure is formed by joining peripheral portions of the thermoplastic spun lace layer and the nonwoven spun lace layer such that the plurality of layers of absorbent material are disposed substantially within an interior cavity of the envelope structure. In certain embodiments, the absorbent material is disposed within the interior cavity of the envelope structure. In certain embodiments, the absorbent material comprises carboxymethylated cellulose fibers. In some instances, the wound contact layer comprises carboxymethylated cellulose fibers. In some instances, the wound contact layer comprises reinforcing nylon stitching. In some instances, the pressure dispersion layer comprises reticulated foam.

In certain embodiments, the wound exudate management systems disclosed herein further comprises fenestrations in the one or more of the plurality of layers of absorbent material. In certain embodiments, the wound exudate management systems further comprise a pressure conveyance disposed within the flexible connector. In some embodiments, the wound exudate management systems further comprise an absorbent indicator and an adhesive member, wherein the adhesive member adheres the flexible connector and the absorbent indicator to the wound dressing. In some embodiments, the absorbent indicator of the wound exudate management systems disclosed herein is positioned in the pathway at a location between the absorbent layer and the flexible connector, the absorbent indicator is capable of absorbing exudate to indicate the presence of exudate at the side of the absorbent layer furthest from the wound. In some embodiments, the absorbent indicator gives a visual indication of the presence of exudate at the side of the absorbent layer furthest from the wound. In some embodiments, the wound exudate management systems disclosed herein further comprise a status indicator, the status indicator providing visual cues indicating when the pump is off, on, or on but malfunctioning.

Also disclosed herein are methods and processes of using an inline filter to maintain a negative pressure of a wound dressing and protect a wound exudate management system from wound exudate, the method comprising obtaining the inline filter comprising an inlet opening, an outlet opening, and a cartridge flanked by the inlet and outlet openings, the cartridge comprising a cavity housing a one-way check valve and at least one filter membrane; connecting the outlet opening to a first pressure tube, wherein the first pressure tube is connected to a pump on the opposite end of the first pressure tube that is connected to the outlet opening; connecting the inlet opening to a second pressure tube, wherein the second pressure tube is connected to the wound dressing on the opposite end of the second pressure tube that is connected to the inlet opening; and generating negative pressure in the wound dressing by actuating the pump to draw air away from the wound dressing. In some embodiments, the pump maintains a negative pressure between 40 mmHg and 200 mmHg in the wound dressing. In some embodiments, the pump maintains a negative pressure of 80 mmHg in the wound dressing. In some embodiments, the pump maintains a negative pressure between 100 mmHg and 150 mmHg. In some embodiments, the pump maintains a negative pressure of 125 mmHg in the wound dressing. In some instances, the wound exudate is absorbed and prevented from entering the pump by the at least one filter membrane of the inline filter. In some instances, the pump comprises a status indicator providing visual cues indicating when the pump is off, on, or on but malfunctioning. In some embodiments, the malfunctioning of the pump is triggered by a negative pressure outside of the negative pressure range between 40 mmHg to 200 mmHg in the wound dressing, or between 100 mmHg to 150 mmHg in the wound dressing.

BRIEF DESCRIPTION OF THE FIGURES

FIG. 1A shows an image of an exemplary inline filter (left-hand side of the image) next to a luer fitting without an inline filter (right-hand side of the image). FIG. 1B shows a cutaway view of a design of an exemplary inline filter as disclosed herein. Fluid flows from left to right in the orientation shown in FIG. 1B.

DETAILED DESCRIPTION OF ILLUSTRATIVE EMBODIMENTS

Figure 1A:
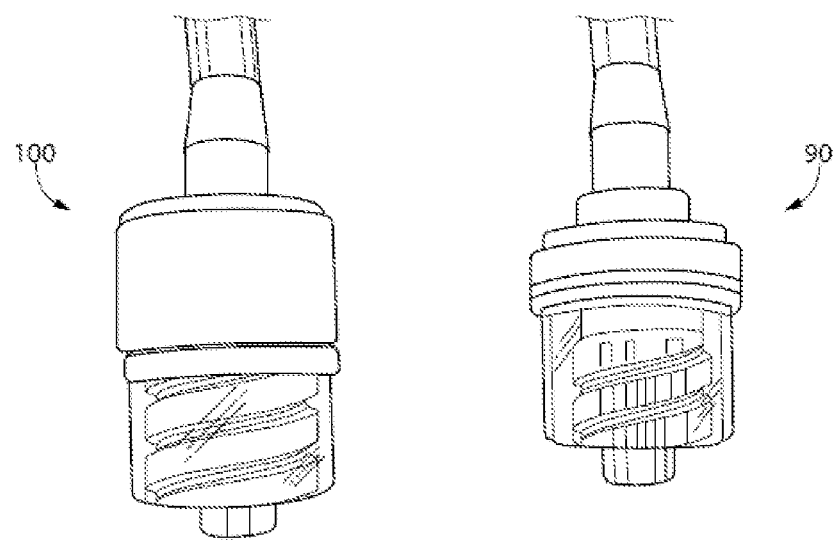
FIGS. 1A and 1B show embodiments of the inline filters disclosed herein.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described.

Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Items listed in the form of "A, B, and/or C" can also mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

In the drawings, some structural or method features may be shown in certain specific arrangements and/or orderings. However, it should be appreciated that such specific arrangements and/or orderings may not necessarily be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may be omitted or may be combined with other features.

Provided herein, in some embodiments, are inline filters, including inline filters suitable for use in negative-pressure wound therapy (NPWT) systems and inline filters suitable for use in wound exudate management systems treating various types of wounds. In some embodiments, the wound exudate management system comprises a wound dressing and a portable pump. In some embodiments, the wound exudate management system creates and maintains a negative pressure at the site of the wound as part of the NPWT. In some embodiments, a wound dressing is applied to a site of a wound as part of a wound exudate management system comprising a portable pump, and a negative pressure is exerted and maintained on the wound by the portable pump. Adequate levels of negative pressure in the wound dressing can be continuously monitored by the pump, and the inline filter prevents excess exudate from entering the pump and or its associated tubing.

Also provided herein are compositions comprising inline filters for use with a wound exudate management system and methods of using the inline filter as part of the wound exudate management system to treat various types of wounds. In some embodiments, the inline filter disclosed herein comprises an inlet opening having a fitting or tube connector, an outlet opening having a fitting or tube connector, and a cartridge flanked by the inlet and outlet openings. In some embodiments, the cartridge comprises a cavity, a one-way check valve, and at least one filter membrane. In some embodiments, the one-way check valve and the at least one filter membrane are housed inside the cavity of the cartridge and perpendicular to the inlet opening and the outlet opening. In some embodiments, the at least one filter membrane is positioned between the inlet opening and the one-way check valve. In some embodiments, the at least one filter membrane is positioned between the one-way check valve and the outlet opening. In some embodiments, a first filter membrane is positioned between the inlet opening and the one-way check valve, and a second filter membrane is positioned between the one-way check valve and the outlet opening. In some instances, disclosed herein are inline filters comprising filter membranes comprising hydrophilic material. In some instances, disclosed herein are inline filters comprising filter membranes comprising hydrophobic material. In some embodiments, the inline filters disclosed herein comprise a pore size of at least 0.15 microns, 0.2 microns, 0.3 microns, 0.4 microns, 0.5 microns, 0.6 microns, 0.7 microns, 0.8 microns, 0.9 microns, 1.0 microns, 1.1 microns, 1.2 microns, 1.3 microns, 1.4 microns, 1.5 microns, 1.6 microns, 1.7 microns, 1.8 microns, 1.9 microns, 2.0 microns, 2.1 microns, 2.2 microns, 2.3 microns, 2.4 microns, 2.5 microns, 2.6 microns, 2.7 microns, 2.8 microns, 2.9 microns, 3.0 microns, 3.1 microns, 3.2 microns, 3.3 microns, 3.4 microns, 3.5 microns, 3.6 microns, 3.7 microns, 3.8 microns, 3.9 microns, 4.0 microns, 4.5 microns or 5.0 microns.

Disclosed herein, in some embodiments are methods of using the inline filters to maintain a negative pressure of a wound dressing and protect a wound exudate management system from wound exudate. In some embodiments, the wound exudate is absorbed or prevented from entering the pump by the inline filter. In some embodiments, the method of using the inline filters as described herein ensures a negative pressure is achieved and maintained in the wound exudate manage system during use. In some embodiments, the status of the maintenance of negative pressure is monitored by a status indicator.

Illustrated Embodiments

Figure 1B:
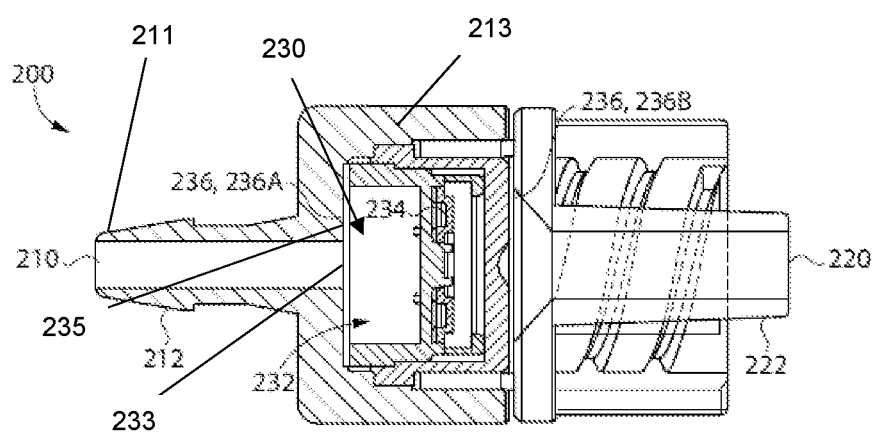

With reference to FIGS. 1A and 1B, illustrated therein are certain embodiments of the inline filters disclosed herein. FIG. 1A shows an image of an exemplary inline filter 100 next to a luer fitting without an inline filter 90. FIG. 1B shows a cutaway view of a design of an exemplary inline filter 200 as disclosed herein. Fluid flows from left to right in the orientation shown in FIG. 1B.

In certain embodiments, the inline filter 200 includes an inlet 211 having an inlet opening 210 having a first connector 212, an outlet opening 220 having a second connector 222, and a cartridge 230 flanked by the inlet opening 210 and the outlet opening 202. The cartridge 230 comprises a cavity 232, a one-way check valve 234, and at least one filter membrane 236. The cartridge 230 is arranged between the inlet opening 210 and the outlet opening 220 in an axial direction. The cavity 232 is formed in a housing 213 of the filter 200 and the inlet 211 is formed in the housing 213 such that the inlet opening 210 extends through the housing 213 to the cavity 232. The at least one filter membrane 236 and the check valve 234 are arranged in the cavity 232 such that the at least one filter membrane 236 and the check valve 234 are at least partially surrounded by the housing 213 in the axial direction. The inlet opening 210 has a constant diameter in the axial direction. The inlet opening 210 opens into the cavity 232 at a cavity inlet 233 of the cavity 232. The filter membrane 236A is located at, and aligned in the axial direction with, the cavity inlet 233 of the cavity 232. The cavity inlet 233 is at least partially defined by a planar interior surface 235 of the housing 213. The filter membrane 236A is in direct contact with the planar interior surface 235.

In certain embodiments, the one-way check valve 234 and the at least one filter membrane 236 are housed inside the cavity 232 and perpendicular to the inlet opening 210 and the outlet opening 220.

In certain embodiments, the at least one filter membrane 236 is positioned between the one-way check valve 234 and the outlet opening 220. Additionally or alternatively, the at least one filter membrane 236 may be positioned between the inlet opening 210 and the one-way check valve 234. In certain embodiments, the filter membrane 236 comprises a pore size of at least 0.2 microns.

In certain embodiments, the filter membrane 236 comprises hydrophilic material. The hydrophilic material may, for example, comprise silver, aluminum, cellulose acetate, ceramic, glass fiber, mixed cellulose ester (MCE), nylon, polyacrylonitrile (PAN), hydrophilic polycarbonate (PCTE), hydrophilic polytetrafluoroethylene (PTFE), hydrophilic polyvinylidene difluoride (PVDF), nitrocellulose, or hydrophilic glass fiber.

In certain embodiments, wherein the at least one filter membrane 236 comprises hydrophobic material. The hydrophobic material may, for example, comprise polyether ether ketone (PEEK), hydrophobic polycarbonate (PCTE), polyethersulfone (PESU), polyester (PETE), polypropylene, hydrophobic polytetrafluoroethylene (PTFE), hydrophobic polyvinylidene difluoride (PVDF), or hydrophobic glass fiber.

Figure 2:
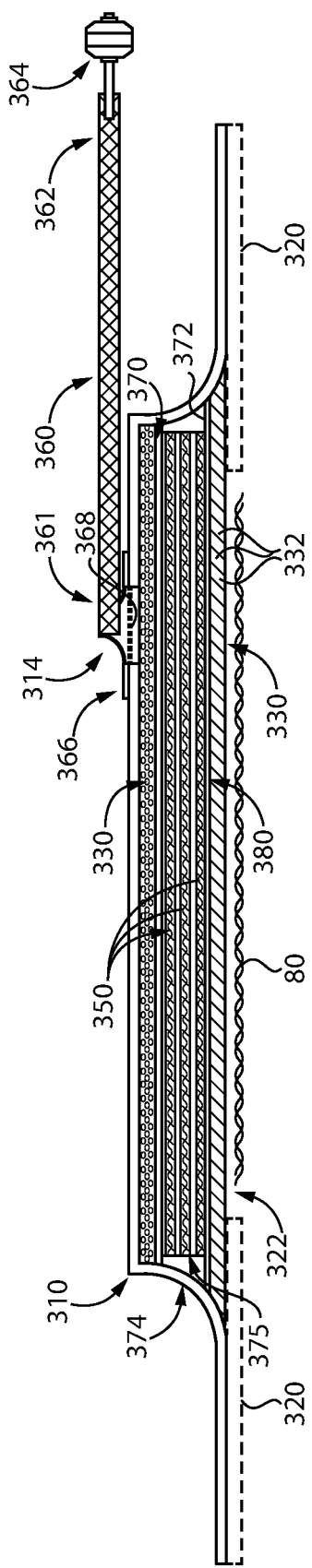
FIG. 2 is a schematic of an exemplary wound dressing for use in combination with the inline filters disclosed here.
Figure 3:
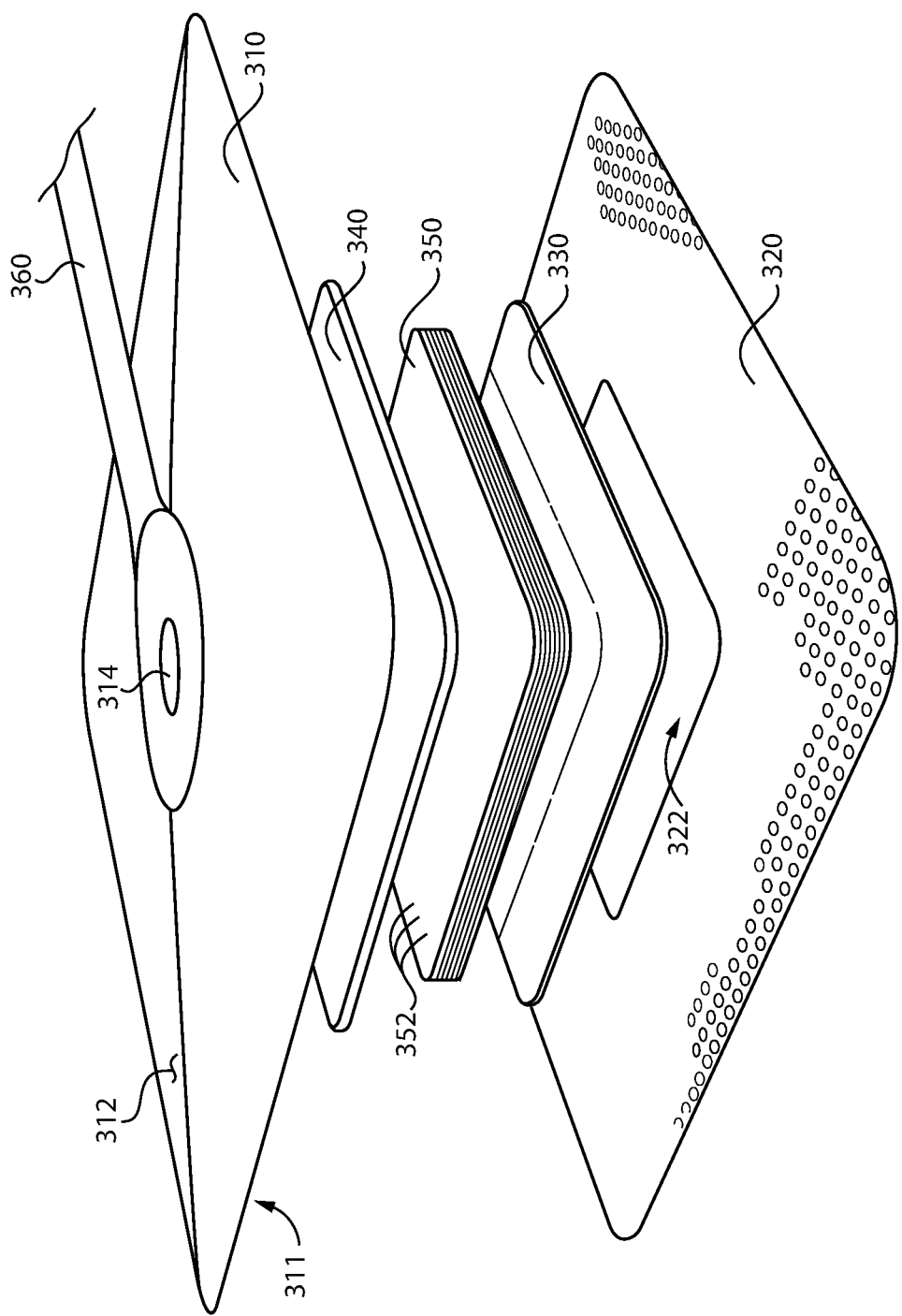
FIG. 3 is an exploded view of the exemplary wound dressing illustrated in FIG. 2.

With additional reference to FIGS. 2 and 3, illustrated therein is a schematic of an exemplary wound dressing 300 for use in combination with the inline filters disclosed here.

The illustrated wound dressing 300 generally includes a backing layer 310 and an adhesive layer 320 for adhering the wound dressing 300 adjacent the wound. In certain embodiments, the wound dressing 300 further comprises a wound contact layer 330 for contacting the wound, a pressure dispersion layer 340, a plurality of absorbent material layers 350 disposed between the wound contact layer 330 and the pressure dispersion layer 340.

The backing layer 310 has a first surface 311 and a second surface 312, and the first surface 351 is adjacent, and in contact with, the pressure dispersion layer 340 and the adhesive layer 320. In certain embodiments, the backing layer 310 is formed of a polyurethane film. The backing layer 310 comprises a port 314 through which exudate may flow to a tube 360.

The adhesive layer 320 generally defines a border about an opening 322 for receiving the wound. In certain embodiments, the adhesive layer 320 comprises a silicone adhesive. In certain embodiments, the adhesive layer 320 may be perforated.

The wound contact layer 330 overlaps the border defined by the adhesive layer 320, and is configured to contact the wound via the opening 322. In certain embodiments, the wound contact layer 330 may comprise Medicel™. In certain embodiments, the wound contact layer 330 comprises carboxymethylated cellulose fibers. In certain embodiments, the wound contact layer 330 may comprise HYDROFIBER®. In certain embodiments, the wound contact layer 330 may be reinforced, for example via nylon stitching. Thus, the wound contact layer 330 may comprise reinforcing nylon stitching 332.

The pressure dispersion layer 340 is adjacent and in contact with the first surface 311 of the backing 310. In certain embodiments, the pressure dispersion layer 340 may be provided as a polyester foam layer. In certain embodiments, the pressure dispersion layer 340 comprises reticulated foam.

The absorbent material layers 350 are positioned between the wound contact layer 330 and the pressure dispersion layer 340. The wound dressing 300 may, for example, comprise eight absorbent material layers 350. In certain embodiments, one or more of the absorbent material layers 350 may comprise carboxymethylated cellulose fibers. In certain embodiments, one or more of the absorbent material layers 350 may comprise Medicel™. In certain embodiments, one or more of the absorbent material layers 350 may comprise HYDROFIBER®. In certain embodiments, one or more of the absorbent material layers 350 further comprises fenestrations 352.

The tube 360 is connected with the port 314 in the backing layer 310. An adhesive ring 366 may form a seal between one end 361 of the tube 360 and the port 314. The opposite end 362 of the tube 360 may be connected with a fitting such as a Luer lock 364. A disc 368, such as one comprising Medicel™, may be positioned in the port 314.

Figure 4:
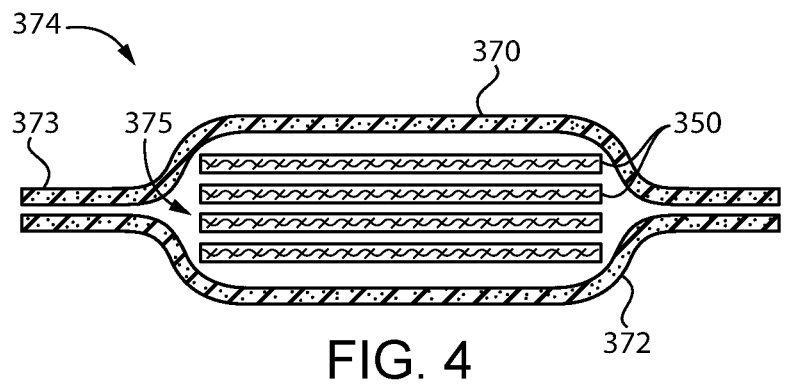
FIG. 4 is a cross-sectional view of a portion of the wound dressing illustrated in FIG. 2.

In certain embodiments, the wound dressing 300 may include an additional layer 370 between the pressure dispersion layer 330 and the uppermost absorbent layer 350. The additional layer 370 may, for example, be formed of thermoplastic. In certain embodiments, the additional layer 370 may be provided as a thermoplastic spun lace layer. In certain embodiments, the wound dressing 300 may further comprise a nonwoven spun lace layer 372 connected to the wound contact layer 330. In certain embodiments, an envelope structure 374 is formed by joining peripheral portions 373 of the thermoplastic spun lace layer 370 and the nonwoven spun lace layer 372 such that the plurality of absorbent material layers 350 are disposed substantially within an interior cavity 375 of the envelope structure 374, for example as illustrated in FIG. 4. In certain embodiments, the absorbent material layers 350 are disposed within the interior cavity 375 of the envelope structure 374.

In certain embodiments, the wound dressing 300 may include a further layer 380 positioned between the wound contact layer 330 and the lowermost absorbent layer 350. The further layer 380 may, for example, be a polyester/viscose layer.

Figure 5:
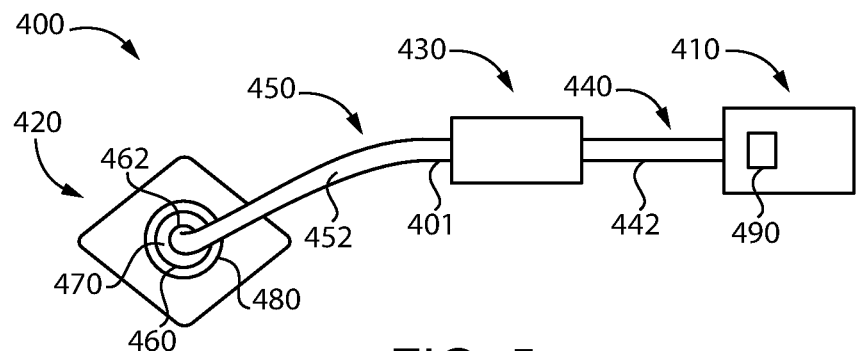
FIG. 5 is a schematic representation of a wound exudate management system according to certain embodiments.

With additional reference to FIG. 5, illustrated therein is a wound exudate management system 400 according to certain embodiments. The wound exudate management system 400 comprises a pump 410 for generating negative pressure, a wound dressing 420 for covering and protecting a wound, an inline filter 430, a first pressure tube 440 having a first interior lumen 442, a second pressure tube 450 having a second interior lumen 452, and a flexible connector 460. The first pressure tube 440 is disposed between the pump 410 and the inline filter 430. The second pressure tube 450 is disposed between the inline filter 430 and the flexible 460. The flexible connector 460 is disposed between the second pressure tube 450 and the wound dressing 420 such that the pump 410 and the wound dressing 420 are in fluid communication via the interior lumens 442, 452. In certain embodiments, the wound dressing 420 may be provided along the lines of the above-described wound dressing 300. In certain embodiments, the inline filter 430 may be provided along the lines of the above-described inline filter 200.

In certain embodiments, a pressure conveyance 462 is disposed within the flexible connector 460.

As described herein, certain embodiments further comprise an absorbent indicator 470, such as the disc 368, and an adhesive member 480 such as the adhesive ring 366. The adhesive member 480 may adhere the flexible connector 460 and the absorbent indicator 480 to the wound dressing 420. In certain embodiments, the absorbent indicator is positioned in a flow pathway at a location between the absorbent layers 350 and the flexible 460. The absorbent indicator 470 is capable of absorbing exudate to indicate the presence of exudate at the side of the absorbent layer 350 furthest from the wound. In certain embodiments, the absorbent indicator 470 gives a visual indication of the presence of exudate at the side of the absorbent layer 350 furthest from the wound.

Certain embodiments of the system 400 further comprise a status indicator 490 configured to provide visual cues indicating when the pump is off, on, and/or on but malfunctioning.

Figure 6:
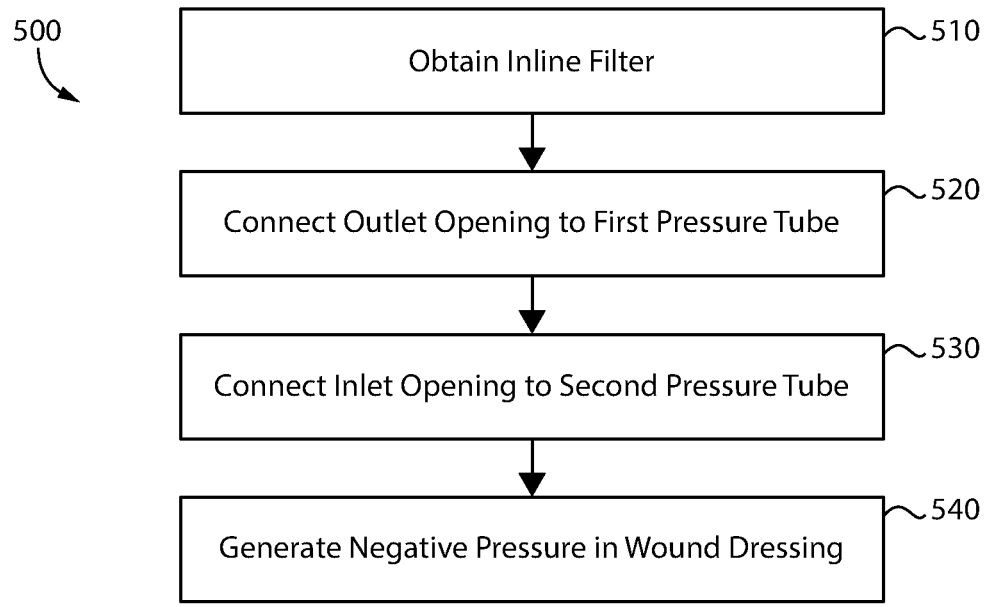
FIG. 6 is a schematic flow diagram of a process according to certain embodiments.

With additional reference to FIG. 6, an exemplary process 500 that may be performed using the system 400 is illustrated. Blocks illustrated for the processes in the present application are understood to be examples only, and blocks may be combined or divided, and added or removed, as well as re-ordered in whole or in part, unless explicitly stated to the contrary. Additionally, while the blocks are illustrated in a relatively serial fashion, it is to be understood that two or more of the blocks may be performed concurrently or in parallel with one another. Moreover, while the process 500 is described herein with specific reference to an implementation of the system 400 in which the inline filter 430 is provided as the inline filter 200 and the dressing 420 is provided in the form of the dressing 300, it is to be appreciated that the process 500 may be performed with inline filters, dressings 300 and/or systems having additional or alternative features.

The process 500 may begin with block 510, which generally involves obtaining an inline filter such as the inline filter 200. The inline filter obtained in block 510 generally comprises an inlet opening 210, an outlet opening 220, and a cartridge 230 flanked by the inlet opening 210 and the outlet openings 220. The cartridge 230 comprises a 232 housing a one-way check valve 234 and at least one filter membrane 236.

The process 500 may include block 520, which generally involve connecting the outlet opening to a first pressure tube. For example, block 520 may involve connecting the outlet opening 220 to the first pressure tube 440, wherein the first pressure tube 440 is connected to a pump 410 on the opposite end of the first pressure tube 440 that is connected to the outlet opening 220.

The process 500 may include block 530, which generally involves connecting the inlet opening to a second pressure tube. For example, block 530 may involve connecting the inlet opening 210 to a second pressure tube 450, wherein the second pressure tube 450 is connected to the wound dressing 300 on the opposite end of the second pressure tube 450 that is connected to the inlet opening 210.

The process 500 may further include block 540, which generally involves generating negative pressure in the wound dressing by actuating the pump to draw air away from the wound dressing. For example, block 540 may involve generating negative pressure in the wound dressing 300/420 by actuating the pump 410 to draw air away from the wound dressing 300/420. In certain embodiments, the pump 410 maintains a negative pressure between 40 mmHg and 125 mmHg in the wound dressing 300/420. In certain embodiments, the pump 410 maintains a negative pressure of 80 mmHg in the wound dressing 300/420. In certain embodiments, the pump maintains a negative pressure of 125 mmHg in the wound dressing 300/420.

In certain embodiments, the wound exudate is absorbed and prevented from entering the pump 410 by the at least one filter membrane 236 of the inline filter 200/430.

In certain embodiments, the pump 410 comprises a status indicator 490 providing visual cues indicating when the pump 410 is off, on, and/or on but malfunctioning. In certain embodiments, the malfunctioning of the pump 410 is triggered by a negative pressure outside of the negative pressure range between 40 mmHg to 125 mmHg in the wound dressing 300/420. In certain embodiments, the malfunctioning of the pump 410 is triggered by a negative pressure outside of the negative pressure range between 100 mmHg to 150 mmHg in the wound dressing 300/420.

Inline Filters

As should be evident from the foregoing, certain embodiments of the present application relate to an inline filter 200 comprising an inlet opening 210 having a fitting or tube connector 212, an outlet opening 220 having a fitting or tube connector 222, and a cartridge 230 flanked by the inlet opening 210 and the outlet opening 220. A non-limiting exemplary list of fitting or tube connector 212, 222 for the inlet and outlet openings 210, 220 include compression fittings, quick disconnect fittings, cam fittings, bite-type fittings, mechanical grip fittings, flare fittings, flange fittings, luer locks, push-to-connect connector, quick coupler, threaded fittings, nipple, barb, and valve. In some embodiments, the fitting or tube connector of the inlet and outlet openings further comprise an adapter, coupling, sleeve, union, cap, plug, reducer, olet, or a combination thereof. In some embodiments, the inlet and outlet openings comprise luer locks to be connected with pressure tubes, where the pressure tubes comprise complementary ends of the luer locks to the inlet and outlet openings. In some instances, the fitting or tube connector of the inlet and outlet openings comprise fitting with added or changed directions such as elbow adapter, 'T' adapter, 'Y' adapter, or cross adapter.

In some embodiments, the cartridge 230 flanked by the inlet and outlet openings 210, 220 comprises a cavity 232 and a one-way check valve 234. In some embodiments, the one-way check valve 234 is housed inside the cavity 232 of the cartridge 230 and perpendicular to the inlet and outlet openings 210, 220. A non-limiting exemplary list of the one-way check valve 234 housed inside the cavity 232 includes diaphragm check valve, swing check valve, tilting disc check valve, plug type check valve, ball type check valve, dual disc check valve, clapper valve, stop check valve, life-check valve, in-line check valve, duckbill valve, and pneumatic non-return valve.

In some embodiments, the cartridge 230 flanked by the inlet and outlet openings 210, 220 comprises a cavity 232, a one-way check valve 234, and at least one filter membrane 236. In some embodiments, the one-way check valve 234 and the at least one filter membrane 236 are housed inside the cavity 232 of the cartridge 230 and perpendicular to the inlet and outlet openings 210, 220. In some embodiments, the at least one filter membrane 236 is positioned between the inlet opening 210 and the one-way check valve 234. In some embodiments, the at least one filter membrane 236 is positioned between the one-way check valve 234 and the outlet opening 220. In some embodiments, a first filter membrane 236A is positioned between the inlet opening 210 and the one-way check valve 234, and a second filter membrane 236B is positioned between the one-way check valve 234 and the outlet opening 220.

In some embodiments, the filter membrane 236 of the inline filter 200 disclosed herein comprises a diameter of less than 50 mm, less than 45 mm, less than 40 mm, less than 35 mm, less than 30 mm, less than 25 mm, less than 24 mm, less than 23 mm, less than 22 mm, less than 21 mm, less than 20 mm, less than 19 mm, less than 18 mm, less than 17 mm, less than 16 mm, less than 15 mm, less than 14 mm, less than 13 mm, less than 12 mm, less than 11 mm, less than 10 mm, less than 9 mm, less than 8 mm, less than 7 mm, less than 6 mm, or less than 5 mm.

In some embodiments, the filter membrane 236 of the inline filter 200 comprises a thickness of less than 50 mm, less than 45 mm, less than 40 mm, less than 35 mm, less than 30 mm, less than 25 mm, less than 24 mm, less than 23 mm, less than 22 mm, less than 21 mm, less than 20 mm, less than 19 mm, less than 18 mm, less than 17 mm, less than 16 mm, less than 15 mm, less than 14 mm, less than 13 mm, less than 12 mm, less than 11 mm, less than 10 mm, less than 9 mm, less than 8 mm, less than 7 mm, less than 6 mm, or less than 5 mm, or less than 4 mm, or less than 3 mm, or less than 2 mm, or less than 1 mm, or less than 0.5 mm, or less than 0.4 mm, or less than 0.3 mm, or less than 0.2 mm, or less than 0.1 mm, or less than 0.05 mm. In some embodiments, the filter membrane 236 of the inline filter 200 comprises a pore size of at least 0.15 microns, 0.2 microns, 0.3 microns, 0.4 microns, 0.5 microns, 0.6 microns, 0.7 microns, 0.8 microns, 0.9 microns, 1.0 microns, 1.1 microns, 1.2 microns, 1.3 microns, 1.4 microns, 1.5 microns, 1.6 microns, 1.7 microns, 1.8 microns, 1.9 microns, 2.0 microns, 2.1 microns, 2.2 microns, 2.3 microns, 2.4 microns, 2.5 microns, 2.6 microns, 2.7 microns, 2.8 microns, 2.9 microns, 3.0 microns, 3.1 microns, 3.2 microns, 3.3 microns, 3.4 microns, 3.5 microns, 3.6 microns, 3.7 microns, 3.8 microns, 3.9 microns, 4.0 microns, 4,5 microns or 5.0 microns.

In some instances, the filter membrane 236 comprises hydrophilic material. Non-limiting examples of hydrophilic material for the filter membrane include silver, aluminum, cellulose acetate, ceramic, glass fiber, mixed cellulose ester (MCE), nylon, polyacrylonitrile (PAN), hydrophilic polycarbonate (PCTE), hydrophilic polytetrafluoroethylene (PTFE), hydrophilic polyvinylidene difluoride (PVDF), nitrocellulose, or hydrophilic glass fiber.

In some instances, the filter membrane 236 comprises hydrophobic material. Non-limiting examples of hydrophobic material for the filter membrane include polyether ether ketone (PEEK), hydrophobic polycarbonate (PCTE), polyethersulfone (PESU), polyester (PETE), polypropylene, hydrophobic polytetrafluoroethylene (PTFE), hydrophobic polyvinylidene difluoride (PVDF), or hydrophobic glass fiber. In some embodiments, the first filter membrane and the second filter membrane comprise of the same material. In some embodiment, the first filter membrane and the second filter membrane comprise of different material.

In some embodiments, the inline filters disclosed herein comply with standards which specify usability requirements for the development of and use of medical devices, such as IEC 62366-1. In some embodiments, the inline filters disclosed herein are biocompatible for their intended use and meet requirements for animal derived components. In some embodiments, the inline filters disclosed herein are configured for one-time use. In some embodiments, the inline filters disclosed herein are configured for use by not more than one patient.

In some embodiments, the inline filters disclosed herein are capable of sterilization. In some embodiments, the inline filters are sterilized by electron beam (E-beam), gamma sterilization or ethylene oxide sterilization. In some embodiments, the inline filters still perform to the desired specification following sterilization. In some embodiments, the inline filters disclosed herein do not comprise latex. In some embodiments, the inline filters disclosed herein do not comprise Bis(2-ethylhexyl) phthalate (DEHP).

In some embodiments, the inline filters disclosed herein comprise an outlet opening 220 with a fitting or a connector 212 that is configured to form an airtight fitting with a first pressure tube 450 connecting the inline filter 200 to a pump portion 410 of a wound exudate management system 400. In some embodiments, the inline filters disclosed herein comprise an inlet opening 210 having a fitting or a connector 212 for forming an airtight connection with a second pressure tube 450 connected to the flexible connector 460, which is connected to a wound dressing 300/420. In some embodiments, the pump 410, first pressure tube 440, inline filter 430, second pressure tube 450, and flexible connector 460 create a continuous lumen 401 in a wound exudate management system 460. Actuation of the pump 410 draws air away from the wound dressing 420, creating a negative pressure in the wound dressing 420 and the continuous lumen 401.

In some embodiments, the inline filters disclosed herein prevent exudate from accidentally entering a first pressure tube connected to a pump, and prevent the pump from malfunctioning. For example, the inline filter 200/430 may prevent exudate from accidentally entering the first pressure tube 440 to thereby prevent the pump 410 from malfunctioning as a result of such exudate. Exudate which comes in contact with the disclosed inline filters 430 may also cause a drop in the negative pressure of the entire wound exudate management system 400 during use. When a drop in negative pressure exceeds a predetermined range, a status indicator 490 on the pump 410 can alert a user regarding potential malfunctioning of the wound exudate system 400, which may result in the user replacing the wound dressing 420 and/or blocked inline filter 430 with a new inline filter 430 in order to restore the negative pressure in the wound dressing 420.

In some embodiments, the inline filters disclosed herein are included with a negative pressure wound dressing system such as the negative pressure wound dressing system 400. In some embodiments, the inline filters disclosed herein comprise inline filter packaging systems. Suitable materials for inline filter packaging systems are easily torn and include, by way of non-limiting examples, paper and waxed paper. In some embodiments, the inline filter packaging system protects the product from physical damage during transit and storage. In some embodiments, the inline filter packaging system is openable by hand. In some embodiments, the inline filter packaging system clearly identifies an opening end. In some embodiments, the inline filter packaging system states shipping and storage conditions between −29° C. and 60° C. In some embodiments, the inline filters disclosed herein are suitable for storage at temperatures between −29° C. and 60° C. In some embodiments, the inline filters disclosed herein have a minimum shelf life of 12 months.

In some embodiments, the inline filters disclosed herein are configured for use as or with a stand-alone infection detection (SID) device. Current practices identifying infection/bioburden in wounds (including clinical signs and microbiology) can be subjective and lead to an incorrect diagnosis. The inline filters disclosed herein can allow early detection of wound infection and lead to faster treatment of infection along with more appropriate use of antibiotics and improved clinical and economic outcomes. In some embodiments, the inline filters are swabbed and the swab is contacted with indicator strips allowing detection of markers of infection such as pH, myeloperoxidase (MPO), and human neutrophil elastase (HNE). In some embodiments, the inline filter is directly contacted with indicator strips allowing detection of markers of infection. In some embodiments, the inline filters disclosed herein comprise a removable cartridge 230 for sampling. In some embodiments, the inline filters disclosed herein comprise a Y-connector or straight inline SID system, or a combination of one or more systems.

Wound Exudate Management System

In some embodiments, provided herein are wound exudate management systems comprising a pump for generating negative pressure, a wound dressing for covering and protecting a wound, an inline filter, a first pressure tube for connecting the pump to the inline filter, and a second pressure tube for connecting the inline filter to a flexible connector. For example, the wound exudate management system 400 comprising a pump 410 for generating negative pressure, a wound dressing 420 for covering and protecting a wound, an inline filter 430, a first pressure tube 440 for connecting the pump 410 to the inline filter 430, and a second pressure tube 450 for connecting the inline filter 430 to a flexible connector 460. The flexible connector 460 is connected to the wound dressing 420 on the opposite end of the flexible connector that is connected to the second pressure tube 450. In some embodiments, the first and/or second pressure tube 440, 450 has a length of 300 mm or more. In some embodiments, the pump unit 410 comprises an indicator 490 which indicates when a target pressure (such as −80 mmHg) is established. In some embodiments, the pump unit 410 comprises an indicator 490 which indicates when a target pressure (such as −80±10 mmHg) is unable to be maintained. In some embodiments, the pump unit 410 establishes negative pressure within 60 seconds following connection to the wound dressing 420.

Certain embodiments relate to a wound exudate management system 400 comprising a pump 410 for generating negative pressure, a wound dressing 420 (e.g., the wound dressing 300) for covering and protecting a wound, first and a second pressure tubes 440, 450 having interior lumens 442, 452, an inline filter 430 (e.g., the inline filter 200) disposed between the pump 410 and the wound dressing 420, a flexible connector 460 connecting the wound dressing 420 to the second pressure tube 450, and an indicator 470 (e.g., the disc 368) disposed between the wound dressing 420 and the flexible connector 460. In some embodiments, the flexible connectors 460 are no more than 25 mm in any dimension. In some embodiments, the total tubing length of the wound exudate management system is no more than 1500 mm, 2000 mm, 2500 mm, 3000 mm, 3500 mm, 4000 mm, 4500 mm, or 5000 mm.

In some embodiments, the pressure tubes 440, 450 between the wound dressing 420 and the pump 410 are able to withstand the maximum negative pressure generated by the pump unit 410 in a fault mode. In some embodiments, disclosed herein are wound exudate management systems comprising a pump for generating negative pressure, wherein the pump 410 comprises a status indicator 490. In some embodiments, the status indicator 490 provides visual cues indicating when the pump is off, on, and/or on but malfunctioning. Malfunctioning includes when the pump 410 is not maintaining a predetermined range of negative pressure. In some embodiments, the pressure created and maintained by the pump 410 during the use of the wound exudate management system is measured barometrically. In some embodiments, the pressure is measured mechanically or digitally.

In some embodiments, the pump 410 comprises a status indicator 490 which indicates if the negative pressure is below about 40 mmHg, about 50 mmHg, about 60 mmHg, about 70 mmHg, about 80 mmHg, about 90 mmHg, about 100 mmHg, about 110 mmHg, about 120 mmHg, about 125 mmHg, about 130 mmHg, about 135 mmHg, about 140 mmHg, about 145 mmHg, or about 150 mmHg. In some embodiments, the pump 410 comprises a status indicator 490 that indicates if the negative pressure is below about 40 mmHg, or above about 200 mmHg. In some embodiments, the pump 410 comprises a status indicator 490 that indicates if the negative pressure is below about 100 mmHg or above about 150 mmHg, for example 125 mmHg. In some embodiments, the pump 410 comprises a status indicator 490 that indicates if the pressure is outside of a set range. In some embodiments, the set range is between about 40 mmHg to about 200 mmHg, between about 40 mmHg to about 150 mmHg, between about 40 mmHg to about 125 mmHg, between about 100 mmHg to about 150 mmHg, for example, 125 mmHg.

In some embodiments, a connection between the pump unit 410 and the wound dressing 420 enables a user to correctly assemble the wound exudate management system 400 (e.g., by connecting the wound dressing 420 to the pump 410). In some embodiments, the one-way check valve 234 housed inside the cartridge 230 of the inline filter 200 maintains the negative pressure in the wound dressing 300/420 when the pump 410 is temporarily disconnected or non-operational.

In some embodiments, provided herein are wound exudate management systems comprising a wound dressing for covering and protecting a wound. In some embodiments, the wound dressing 300/420 covers and protects the wound. In some embodiments, the wound dressing 300/420 comprises absorbent material, absorbs wound exudate, and promotes healing of the wound. In some embodiments, the wound dressing 300/420 comprises an adhesive layer for adhering the wound dressing adjacent the wound.

In some embodiments, the wound dressing 420 of the wound management system 400 comprises a wound contact layer for contacting the wound. For example, the wound dressing 420 may be provided in the form of the wound dressing 300, which comprises a wound contact layer 330 as described above. In some embodiments, the wound dressing of the wound management system optionally comprises a pressure dispersion layer such as the above-described pressure dispersion layer 340. In some embodiments, the wound dressing 420 of the wound management system 400 comprises a plurality of absorbent material layers 350 disposed between the wound contact layer 330 and the pressure dispersion layer 340. In some instances, the wound dressing 300 further comprises a backing layer 310 having a first surface 311 and a second surface 312, wherein the first surface 311 of the backing layer 310 is adjacent and in contact with the pressure dispersion layer 340 and the adhesive layer 320. In some embodiments, the wound exudate management systems described herein comprises a wound dressing which comprises an envelope structure 374 formed by joined peripheral portions 373 of the pressure dispersion layer 340 and the wound contact layer 330.

In some embodiments, provided herein are wound exudate management systems comprising a wound dressing for covering and protecting a wound, wherein the wound dressing for covering and protecting the wound comprises an adhesive layer 320 for adhering the wound dressing adjacent the wound, a wound contact layer 330 for contacting the wound, a pressure dispersion layer 340, a plurality of layers 350 of absorbent material disposed between the wound contact layer 330 and the pressure dispersion layer 340, and a backing layer 310 having a first surface 311 and a second surface 312, wherein the first surface 311 of the backing layer 310 is adjacent and in contact with the pressure dispersion layer 340 and the adhesive layer 320.

In some embodiments, the wound exudate management systems described herein comprise a wound dressing which comprises an envelope structure formed by joined peripheral portions of the pressure dispersion layer and the wound contact layer, wherein the envelope structure defines a cavity. In some instances, the wound exudate management system comprises a wound dressing 300 comprising a thermoplastic spun lace layer 370 connected to a pressure dispersion layer 340, and a nonwoven spun lace layer 372 connected to a wound contact layer 330, wherein an envelope structure 374 is formed by joining peripheral portions 373 of the thermoplastic spun lace layer 370 and the nonwoven spun lace layer 372 such that the plurality of layers 350 of absorbent material are disposed substantially within an interior cavity 375 of the envelope structure 374. In some embodiments, the wound exudate management systems disclosed herein comprise a wound dressing comprising absorbent material disposed within the cavity 375 of an envelope structure 374 formed by joining peripheral portions 373 of the thermoplastic spun lace layer 370 and a nonwoven spun lace layer 372.

In some instances, the wound exudate management systems disclosed herein comprise a wound dressing 300 comprising absorbent material comprising carboxymethylated cellulose fibers. In some embodiments, the wound contact layer 330 of the wound dressing of the wound exudate management systems disclosed herein comprise carboxymethylated cellulose fibers and have reinforcing nylon stitching 332. In some instances, the wound exudate management systems described herein comprise a wound dressing comprising a pressure dispersion layer 340 comprising reticulated foam. In certain instances, the wound exudate management systems disclosed herein further comprise fenestrations 351 in one or more of a plurality of layers 350 of absorbent material in a wound dressing 300 and a pressure conveyance member 462 disposed within a flexible connector 460 connected to a second surface 312 of a backing layer 310 of the wound dressing 300.

In certain embodiments, the pressure conveyance 462 is disposed within the flexible connector 460. The pressure conveyance enables the flexible connector 460 to convey fluid flow and/or pressure within the flexible connector, preventing collapsing when the flexible connector is made of a thin-walled flexible material, thereby enabling the wound dressing to experience or exhibit negative pressure generated by the pump. The pressure conveyance 462 may include various materials including, but not limited to, nylon. Further, the pressure conveyance 462 may be comprised of a lattice structure. The shape, material and arrangement of the pressure conveyance enables continued fluid flow along the flexible connector 460 that may otherwise be hindered by the shape, flexibility, material or arrangement of the flexible connector in light of negative pressure generated by the pump 410 and in light of general wound exudate management system use and positioning.

In some embodiments, the wound exudate management systems disclosed herein comprise an absorbent indicator 470 such as the disk 368 and an adhesive member 480 such as the adhesive ring 366, wherein the adhesive member 480 adheres a flexible connector such as the flexible connector 460 and the absorbent indicator 470 to a backing layer 310 of a wound dressing 300. In some embodiments, the wound exudate management systems disclosed herein comprise an absorbent indicator 368 positioned in a pathway at a location between an absorbent layer 450 of a wound dressing and the flexible connector 460, wherein the absorbent indicator 368/470 is capable of absorbing exudate in order to indicate the presence of exudate at a side of the absorbent layer 350 furthest from a wound 80. In some embodiments, the absorbent 368/470 indicator gives a visual indication of the presence of exudate at the side of the absorbent layer furthest from the wound. In some embodiments, the signal generated by the absorbent indicator absorbing exudate may be visual, audible, vibrational, etc.

Wound Dressings

Disclosed herein, in certain embodiments, are wound dressings configured to function in combination with the inline filters disclosed herein, including wound dressings configured to function in negative pressure wound therapy (NPWT) systems. In some embodiments, the wound dressings disclosed herein limit the transmission of liquid into the pressure tubes, including any part of the wound exudate management system between the medical disc and the pump unit. In some embodiments, the wound dressings disclosed herein can be disconnected from the pump at least once a day for seven days without affecting the system's ability to transmit pressure and handle fluid (including not causing a leak).

In some embodiments, the wound dressings disclosed herein comprise a backing layer such as the backing layer 310. In some embodiments, the wound dressings disclosed herein comprise at least one absorbent layer such as the absorbent layer 350. In some embodiments, the wound dressings disclosed herein comprise a perforated hydrophobic layer and a release liner comprising at least a first edge located opposite to a second edge. In some embodiments, the wound dressings optionally comprise an outer cover layer, which completely overlies the other layers of the wound dressing. In some embodiments, beneath the cover layer is an absorbent pad forming a central raised island beneath the cover layer. In some embodiments, the absorbent pad comprises a plurality of absorbent material layers 350. The absorbent layer is capable of absorbing exudate from a wound. In some embodiments, the outer cover layer covers the side of the absorbent layer furthest from the wound. In some embodiments, the cover layer, also referred to as the backing layer, is adapted to enable negative pressure to be applied at the wound and has a port 314 in fluid communication with the absorbent layer(s) 350. The conduit, or tubing, allows fluid communication between the port and a source of negative pressure, the conduit being connected to the outer layer by an adhesive ring 366.

An indicator means, or absorbent indicator 368, is disposed between the wound dressing 420 and the second pressure tube 450. In some embodiments, the signal generated by the absorbent indicator 368 absorbing exudate may be visual, audible, vibrational, etc. In one embodiment the indicator means comprises a layer of gel forming fibers. Alternatively, the indicator means may also be provided still in the port, but above the cover layer. In some embodiments, the wound dressing further comprises a wound contact layer 330 adhered to the absorbent layer 320 by a layer of heat sealable lace consisting of a polyamide lace layer. The wound dressing can further comprise an exudate and pressure distribution layer, also referred to as a pressure dispersing layer 370, preferably of polyester foam which serves to spread exudate across the absorbent layer(s) 350 and smooth the application of negative pressure across the wound dressing. A further heat sealable lace layer may be provided between the distribution layer and the cover layer. The heat sealable layers assist in adhering the layers together. In some embodiments, the absorbent layer(s) 350, the wound contact layer 330 and the indicator means 368 comprise gel forming fibers in the form of a layer or layers carboxymethylated cellulose fabric.

In some embodiments, the wound dressings configured to function in combination with the inline filters disclosed herein comprise materials suitable for use in bandages. Suitable materials for bandages are non-irritating, durable, and flexible and include, by way of non-limiting examples, textiles of natural fiber (e.g., cotton, linen, and hemp), textiles of synthetic fiber (e.g., nylon, polyester, aramid, olefin, and acrylic), and plastic (e.g., polyvinyl chloride, low-density polyethylene, and polypropylene). In some embodiments, the wound dressings disclosed herein comprise wound dressing packaging and release liner systems. Suitable materials for wound dressing packaging and release liner systems are easily torn and include, by way of non-limiting examples, paper and waxed paper. In some embodiments, the wound dressings disclosed herein are dimensioned to fit different parts of the body, such as wound dressings dimensioned to fit a human finger, or a human knee. In some embodiments, the wound dressings disclosed herein are dimensioned in standard sizes, including for example, 5×5 cm, 6×7 cm, 10×12 cm, 10×20 cm, 15×20 cm, 30×20 cm, 40×20 cm, 50×20 cm, 20×20 cm, 25×25 cm, 30×30 cm, 35×35 cm, 40×40 cm, 45×45 cm, 50×50 cm, or sizes in-between any of these exemplary sizes. In some embodiments, the wound dressings disclosed herein are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 29, 40, 41, 42, 43, 44, 45, 46, 47, 48, 49, 50, or more millimeters long or wide, including increments therein. In some embodiments, the wound dressings disclosed herein are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 29, 40, 41, 42, 43, 44, 45, 46, 47, 48, 49, 50, or more centimeters long or wide, including increments therein. In some embodiments, suitable shapes for the wound dressings disclosed herein include square, rectangular, oval, round, and butterfly-shape wound dressings. In some embodiments, the wound dressings disclosed herein comprise wound dressings with multiple sites for the location of the absorbent layer and multiple sites for the location of the perforated hydrophobic layer.

In some embodiments, the wound dressings configured to function in combination with the inline filters disclosed herein comprise a backing. In some embodiments, the backing is made from polyurethane (PU). In some embodiments, the backing is made from film. In some embodiments, the backing is made from polyurethane film laminated to polyurethane foam. In some embodiments, the polyurethane has a thickness between 0.02 mm and 0.04 mm. In some embodiments, the backing is transparent. In some embodiments, the backing has a high moisture vapor transmission rate (MVTR) and allows moisture to permeate through a wound dressing and evaporate from the wound. In some embodiments, the backing has a MVTR of at least 2,500 grams/meter$^2$/day. In some embodiments, the backing has a MVTR in the range of from 1,000 grams/meter$^2$/day to 30,000 grams/meter$^2$/day, or from 9,000 grams/meter$^2$/day to 27,000 grams/meter$^2$/day. In some embodiments, the MVTR is measured using the liquid in contact ISO standard. In some embodiments, the backing is made from backing film or a strikethrough film.

In some embodiments, the wound dressings configured to function in combination with the inline filters disclosed herein comprise an absorbent layer substantially insoluble in water. In some embodiments, the absorbent layer is a non-adherent layer. In some embodiments, the absorbent layer comprises fiber selected from the group consisting of sodium carboxymethylcellulose fiber, alginate fiber, chitosan or chitosan derivative fiber, acrylic fiber, non-gelling fiber, superabsorbent fiber, and combinations thereof. In some embodiments, the absorbent layer comprises an antimicrobial fiber, such as an antimicrobial fiber comprising silver ions or metal ions. In some embodiments, the wound dressings comprise one or more medicaments selected from the group consisting of an antibiotic, an anesthetic, an anti-inflammatory agent, a skin protective agent, and an odor-absorbing agent. In some embodiments, the fiber comprises chemically modified cellulose. In some embodiments, the fiber is carboxymethylcellulose fiber with a degree of substitution between 0.1 and 0.5 carboxymethyl groups per cellulose unit. In some embodiments, the fiber is an acrylic fiber which incorporates a co-monomer and provides dye-sites in the fiber. In some embodiments, the co-monomer is selected from the group consisting of itaconic acid and 2-acrylamido methyl propane sulphonic acid. Where the fiber is an alginate fiber, it may be a calcium alginate fiber or a mixed metal alginate fiber such as a calcium/sodium alginate fiber. The alginate polymer may be one with a high mannuoronate or a high guluronate. In some embodiments, the wound dressings comprise an absorbent layer comprising chemically modified cellulose. In some embodiments, the wound dressings comprise an absorbent layer comprising, for example, carboxymethylcellulose, carboxyethylcellulose, or other chemically modified cellulose. In some embodiments, the carboxymethylcellulose is sodium carboxymethylcellulose. In some embodiments, the absorbent layer comprises HYDROFIBER® (ConvaTec, United Kingdom).

In some embodiments, the wound dressings described herein provide advantages to the healing of the wound including the advantages of locking in exudate and trapping bacteria (including advantages such as protecting periwound skin and reducing maceration and minimizing wound and cross-infection during wound dressing removal), micro-contouring to a wound bed (including advantages such as minimizing "dead space" where bacteria can grow and maintaining the moisture balance in the wound bed), and responding to wound fluid levels forming a cohesive gel (including advantages such as forming a cohesive gel when the wound dressing comes in contact with exudates and providing a rapid and sustained antimicrobial activity on demand, such as when the wound dressing comprises ionic silver).

In some embodiments, the wound dressings configured to function in combination with the inline filters disclosed herein absorb exudate from a wound. In some embodiments, the wound dressings described herein comprise an absorbent layer with a minimum level of absorbency. In some embodiments, the absorbency of the wound dressings described herein may be measured by the free swell absorbency method. In some embodiments, the absorbency of the wound dressings described herein is at least 0.30 g/cm$_2$, or at least 0.40 g/cm$^2$, or at least 0.50 g/cm$^2$. In some embodiments, the wound dressings are configured to handle 1.1 mL/cm$^2$/day of fluid for three days without the need for a canister to collect the exudate (such as for moderately exuding wounds). In some embodiments, the wound dressings are configured to handle 0.6 mL/cm$^2$/day of fluid for seven days without the need for a canister to collect the exudate (such as for low exuding wounds). In some embodiments, the wound dressings described herein comprise a gelling fiber, an absorbent fiber, or a hydrophilic foam.

In some embodiments, the wound dressings disclosed herein comprise an absorbent core comprising a material selected from the group consisting of foam, polyurethane foam, absorbent textiles, hydrogels, superabsorbent fibers, superabsorbent powder-fiber blends, and mixtures thereof. In some embodiments, the absorbent core comprises a gelling blend of a material selected from the group consisting of foam, polyurethane foam, absorbent textiles, hydrogels, superabsorbent fibers, superabsorbent powder-fiber blends, and mixtures thereof. In some embodiments, the absorbent core comprises a non-gelling blend of a material selected from the group consisting of foam, polyurethane foam, absorbent textiles, hydrogels, superabsorbent fibers, superabsorbent powder-fiber blends, and mixtures thereof. In some embodiments, the wound dressings disclosed herein comprise an absorbent hydrophilic layer comprising a material selected from the group consisting of HYDROFIBER® (ConvaTec, United Kingdom), gelling fiber, gelling fiber blend, gelling fiber—synthetic fiber blend, superabsorbent fiber, superabsorbent powder-fiber blend, and mixtures thereof.

In some embodiments, the wound dressings configured to function in combination with the inline filters disclosed herein comprise a perforated adherent layer, such as the adhesive layer 320. In some embodiments, the perforated adherent layer comprises a perforated hydrophobic layer. In some embodiments, the perforated adherent layer is not hydrophobic, as may be the case when the perforated adherent layer comprises a hydrogel adhesive. In some embodiments, the wound dressings described herein comprise an adherent or hydrophobic layer selected from the group consisting of an adherent or hydrophobic layer comprising cuts, an adherent or hydrophobic layer comprising slits, an adherent or hydrophobic layer comprising holes, an adherent or hydrophobic layer comprising apertures, an adherent or hydrophobic layer comprising discontinuities, and an adherent or hydrophobic layer comprising bevels. In some embodiments, the perforated adherent layer or perforated hydrophobic layer is selected from the group consisting of silicone adhesive, hydrocolloid adhesive, polyurethane adhesive, rubber-based adhesive, acrylic adhesive, coated woven material, hydrogel adhesive, and combinations thereof. In some embodiments, the distribution and spacing of the perforations are regularly arranged with a separation substantially greater than their area. In some embodiments, the perforations are in a shape selected from a circle, a square, a rectangle, a triangle, an oval, a pentagon, a hexagon, and a rounded rectangle. In some embodiments, the perforations are circular and between 0.1 mm and 5 mm, or between 0.5 mm and 2 mm. In some embodiments, the spacing between the perforations is between 0.2 mm and 10 mm. In some embodiments, the number of perforations per unit area is between 1 and 100, or between 1 and 50, or between 1 and 20 perforations/cm$^2$. In some embodiments, the wound dressings disclosed herein comprise an open structure, hydrophobic layer comprising a material selected from the group consisting of silicone adhesive, hydrocolloid adhesive, polyurethane adhesive, hydrogel, acrylic adhesive, coated woven material, and mixtures thereof.

In some embodiments, the wound dressings configured to function in combination with the inline filters disclosed herein comprise an adhesive surrounding the absorbent layer that adheres the wound dressing to the wound. In some embodiments, the absorbent layer is a non-adherent layer. The adhesive holds the absorbent component in direct contact with the wound and may seal the wound dressing to the skin surrounding the wound. The adhesive is preferably a silicone adhesive and more preferably a pressure sensitive silicone adhesive such as Dow Corning MD7-4502 or M67-9900 (DowDuPont, USA) or Wacker Chemie AG SIL-PURAN® 2114 (Wacker Chemie, Germany). The adhesive may also be a hydrocolloid, polyurethane, rubber based adhesive or acrylic adhesive.

In some embodiments, the wound dressings configured to function in combination with the inline filters disclosed herein comprise a foam layer. The foam layer can be an open cell foam layer. The foam layer can be a hydrophilic foam layer. In some embodiments, the hydrophilic foam layer is a polyurethane foam, such as a hydrophilic open celled foam. The foam typically has a thickness of 0.25 mm to 5 mm, preferably from 1 mm to 4.0 mm and most preferably from 1.5 mm to 3 mm. The foam layer preferably has an absorbency of 10 to 20 g/g when measured by the free swell absorptive capacity method. In some embodiments, the foam layer includes a metal-based antimicrobial agent that undergoes a controlled release when the binder layer comes into contact with moisture. In some embodiments, the foam layer includes an inorganic antimicrobial agent. In some embodiments, the foam layer does not include an inorganic antimicrobial agent.

The foam layer may be bonded to the wound contacting layer preferably by a polymer based melt layer, by an adhesive, by flame lamination or by ultrasound, or by curing directly to the foam layer. The foam layer may be directly bonded to the wound contact layer to make a laminate structure where the layers co-extend and are separated by the bonding line or the foam layer may form an island in the upper surface of the component surrounded by the wound contacting layer. By forming an island of foam in the upper surface of the absorbent component in this way, the tendency of the foam to laterally spread the exudate in the foam layer and rewet the wound contacting layer can be physically limited.

A textile layer may be positioned between the wound contact layer and the foam layer to limit distortion of the component that may occur when the foam layer expands on absorption of exudate. The textile layer is preferably made from absorbent fibers such as polyester, nylon, or cotton which may contain superabsorbent components such as cross linked sodium polyacrylate or may be made from a superabsorbent fiber such as polyacrylate.

In some embodiments, a one-way wicking layer is positioned between the wound contact layer and the foam layer to assist in the prevention of exudate rewetting the wound contact layer outside the area of the wound by transfer down from the foam towards the wound. The one-way wicking layer has the property that it resists the passage of exudate in one direction. The one-way wicking layer may, for example, be an embossed perforated film made from ethylene-methyl acrylate/ethylene vinyl acetate.

Methods of Using the Inline Filter

In some embodiments, disclosed herein are methods of using an inline filter to maintain negative pressure in a wound dressing and protect a wound exudate management system from wound exudate. In some embodiments, the wound exudate is absorbed by the inline filters disclosed herein and prevented from entering a pump by a filter membrane in the inline filter. In some embodiments, the methods of protecting a wound exudate management system disclosed herein comprise obtaining an inline filter 200 comprising an inlet opening 210, an outlet opening 220, a one-way check valve 234, and at least one filter membrane 236; connecting the outlet opening 220 to a first pressure tube 440, wherein the first pressure tube 440 is connected to a pump 410 in the wound exudate management system 400 on the opposite end of the first pressure tube 440 that is connected to the outlet opening 220 of the inline filter 200; connecting the inlet opening 210 to a second pressure tube 450, wherein the second pressure tube is connected to the wound dressing 300 on the opposite end of the second pressure tube 450 that is connected to the inlet opening 210 of the inline filter 200; generating a negative pressure in the wound dressing 300 by actuating the pump 410 of the wound exudate management system 400 and drawing air away from the wound dressing 300.

In some instances, the pump 410 maintains a negative pressure between 60 mmHg to 125 mmHg in the wound dressing 300/420. In some embodiments, the one-way check valve 234 housed inside the cartridge 230 of the inline filter is able to maintain a negative pressure of 80±20 mmHg across the wound dressing pad area when the wound dressing 300/420 is disconnected from the pump 410. In some embodiments, the one-way check valve 234 housed inside the cartridge 230 of the inline filter 200 is able to maintain a negative pressure of 80±20 mmHg across the wound dressing pad area when the wound dressing 300/420 is disconnected from the pump 410 for at least 1 hour, 2 hours, 3 hours, 6 hours, 12 hours, 24 hours, 36 hours, 48 hours, or 72 hours. In some embodiments, the pump 410 further comprises a status indicator 490 providing visual cues indicating when the pump 410 is off, on, and/or on but malfunctioning. In some embodiments, malfunctioning of the pump 410 is caused by the pump 410 sensing a negative pressure outside of the negative pressure range between 40 mmHg to 200 mmHg in the wound dressing 300/420. In some embodiments, malfunctioning of the pump 410 is caused by the pump 410 sensing a negative pressure outside of the negative pressure range between 100 mmHg to 150 mmHg, for example, outside of 125 mmHg.

Methods of Treating Wounds

In some embodiments, provided herein are methods of treating wounds by applying negative pressure to a wound dressing covering a wound. In some embodiments, methods disclosed herein are suitable for treating moderately exuding wounds. In some embodiments, the methods disclosed herein are suitable for treating low exuding wounds. In some embodiments, the level of exudate from a wound is determined by weighing soiled wound dressings before and after application to a wound. In some embodiments, the level of exudate from a wound is determined by measuring the contents of wound drainage bags or canisters. In some embodiments, the level of exudate from a wound is determined based on the saturation of a wound dressing at specific intervals, such as every 24 or 48 hours. In some embodiments, the level of exudate from a wound is determined based on the appearance of the wound bed. For example, when a wound is highly exuding, the skin around the wound may be macerated and can be recognized by a whitish, plump, or soggy appearance which breaks down easily and can result in an increase in the overall size of the wound. Alternatively, for non- to low-exuding wounds, the determination may be made by identifying that a wound dressing has dehydrated and caused a slight adhesion to the wound bed, in which case the wound dressing must be hydrated with fluid (such as saline) in order to allow removal of the wound dressing without discomfort to the patient.

In some embodiments, the methods of treating wounds comprises using the wound exudate management system 400 to exert and maintain a negative pressure in the wound dressing 420/300 contacted with the wound 80. In some embodiments, the wound exudate management system 400 comprises an absorbent indicator 368/470 disposed between the wound dressing 300/420 and the second pressure tube 450. The absorbent indicator signals the exudate being absorbed beyond the capacity of the wound dressing 300/420. In some embodiments, the signal generated by the absorbent indicator absorbing exudate may be visual, audible, vibrational, etc.

In some embodiments, the methods of treating wounds disclosed herein comprise of monitoring whether the wound exudate has reached and been absorbed by inline filter, creating a partial blockage in the lumen 401 connecting the wound dressings 300/420 to the pump 410. In some embodiments, the methods of treating wounds comprises monitoring the status indicator 490 on the pump 410. A partial blockage of exudate by the inline filter 200/430 drops negative pressure to below the predetermined negative pressure range.

Example 1

An example of treatment of a wound with a wound exudate management system will now be described. A medical care provider obtains a wound dressing 300 for use in a negative pressure wound therapy system 400. The wound dressing 300 includes a silicone adhesive border 320 with a centrally placed absorbent pad 450 covered by a Polyurethane film 410, and contains an integral flexible airway sited over a Medicel™ disc 368, which is in direct contact with the absorbent pads 350 and attached via an adhesive ring 366. The opposite end of the airway is fitted with a luer fitting 364 comprising an inline filter 200, which enables attachment of the wound dressing 300 to the pump tubing supplied with the pump unit 410. The medical care provider covers the patient's wound 80 with the wound dressing 300. The actuation of the pump 410 exerts negative pressure in the wound dressing 300/420. Contemporaneously, the dressings are highly saturated with exudate. Exudate enters the tubing 450 connecting the dressing 300 to the pump 410 but is prevented from reaching the pump by the inline filter 200/430. The blockage of the inline filter 200/430 by exudate disrupts airflow and causes a drop in negative pressure in the wound dressing 300/420. As a result of the loss of suction in the dressing 300/420, the dressing 300/420 no longer closely conforms to the wound and/or the periwound area, which provides a visual indication to the medical care provider that the inline filter 200/430 is in need of change. The medical care provider replaces the wound dressing 300 comprising the blocked inline filter 200 with a new wound dressing 300/420 containing an inline filter and reconnects the tubing disposed among the wound dressings, inline filter, and pump.

Example 2

Another example involves the testing of certain negative pressure wound therapy systems to evaluate the efficacy of the systems and methods described herein. As a first baseline, a negative pressure wound therapy system was initially tested without an inline filter being utilized. More particularly, the first baseline evaluation involved the use of a conventional luer lock fitting to connect a wound dressing to a pump for providing a negative pressure. Each luer lock fitting was provided with a check valve to prevent leakage of air in the dressing, but was not provided with any filter. With no filter present, exudate was able to pass through the luer lock and into the pump. After a trial period of three days, 100% of the baseline systems experienced exudate in the pump, often leading to damage of the pump.

In a second baseline trial, the luer lock fittings were provided with a first filter, which was formed of PTFE with an average pore size of about 0.2 microns. A new test method involving direct contact of the wound dressing with a test solution was developed in order to facilitate rapid testing of the filters. The filters evaluated in this stage of testing exhibited a pass rate of about 88%. While an improved result over the 0% pass rate for conventional fittings lacking filters, there remained a need for improvement.

A third trial involved the use of glass silicone membranes having an average pore size of about 0.2 microns. A first group of these filters was tested prior to sterilization, and a second group was evaluated following sterilization according to the ethylene oxide (EO) method of sterilization. While the non-sterilized filters performed well in this test, with a pass rate of 100%, it was unexpectedly found that sterilizing the filters led to a degradation in performance. More particularly, filters sterilized according to the EO method of sterilization were found to have a pass rate of just 60%. While an improvement over the 0% pass rate for conventional fittings, the sterilized group lacked the performance of the second baseline trial. As such, there remained a further need for improvement.

A fourth trial involved evaluation of a filter according to certain embodiments of the present application. The filters evaluated in this trial were formed of PESU, and a larger average pore size of about 3 microns was selected. Again, both sterile and non-sterile filters were evaluated. In this case, both the non-sterile filters and the filters sterilized by EO sterilization were found to have a 100% pass rate. Thus, contrary to expectations, the filters having the larger average pore size were found to have improved exudate-blocking characteristics in comparison to the filters evaluated in the second and third trials, each of which had smaller average pore sizes.

Further Examples

Certain embodiments of the present application relate to a wound dressing, comprising: an adhesive layer for adhering the wound dressing adjacent to a wound; a wound contact layer for contacting the wound; a pressure dispersion layer; a plurality of layers of absorbent material disposed between the wound contact layer and the pressure dispersion layer, wherein the plurality of layers of absorbent material includes a first absorbent material layer facing the wound contact layer and a second absorbent material layer facing the pressure dispersion layer; a backing layer having a first surface and a second surface, the first surface of the backing layer being adjacent, and in contact with, the pressure dispersion layer and the adhesive layer, wherein a port is defined in the backing layer; and an absorbent indicator aligned with the port, the absorbent indicator configured to absorb exudate to indicate the presence of exudate in the second absorbent material layer.

In certain embodiments, the wound dressing further comprises an envelope structure defining a cavity; wherein the plurality of layers of absorbent material are received within the cavity. In certain embodiments, the envelope structure is defined at least in part by the pressure dispersion layer and the wound contact layer; and peripheries of the pressure dispersion layer and the wound contact layer are joined to at least partially define the envelope structure.

In certain embodiments, the wound dressing further comprises: a flexible connector mounted adjacent the port; and a tube having a first end connected with the flexible connector and an opposite second end. In certain embodiments, the wound dressing further comprises an inline filter coupled to the second end of the tube. In certain embodiments, the absorbent indicator is visible through the flexible connector. In certain embodiments, the wound dressing further comprises a pressure conveyance coupled to the flexible connector.

In certain embodiments, the wound dressing further comprises: a nonwoven spun lace layer positioned between the wound contact layer and the first absorbent material layer; and a thermoplastic spun lace layer positioned between the pressure dispersion layer and the second absorbent material layer. In certain embodiments, peripheries of the nonwoven spun lace layer and the thermoplastic spun lace layer are joined to define an envelope structure in which the plurality of layers of absorbent material are disposed.

Certain embodiments of the present application relate to a wound exudate management system, comprising: a pump for generating negative pressure; a wound dressing for covering and protecting a wound; a first pressure tube having a first interior lumen; a second pressure tube having a second interior lumen; an inline filter disposed between the first pressure tube and the second pressure tube; and a flexible connector; wherein the first pressure tube is disposed between the pump and the inline filter; wherein the second pressure tube is disposed between the inline filter and the flexible connector; and wherein the flexible connector is disposed between the second pressure tube and the wound dressing such that the pump and the wound dressing are in fluid communication via the interior lumens and the inline filter.

In certain embodiments, the wound dressing comprises an adhesive layer for adhering the wound dressing adjacent to a wound. In certain embodiments, the wound dressing comprises: a wound contact layer for contacting a wound; a pressure dispersion layer; a plurality of layers of absorbent material disposed between the wound contact layer and the pressure dispersion layer; and a backing layer having a first surface and a second surface, the first surface of the backing layer being adjacent, and in contact with, the pressure dispersion layer and an adhesive layer. In certain embodiments, the wound dressing further comprises: a thermoplastic spun lace layer connected to the pressure dispersion layer; and a nonwoven spun lace layer connected to the wound contact layer; wherein an envelope structure is formed by joining peripheral portions of the thermoplastic spun lace layer and the nonwoven spun lace layer such that the plurality of layers of absorbent material are disposed substantially within an interior cavity of the envelope structure. In certain embodiments, the absorbent material is disposed within the interior cavity of the envelope structure. In certain embodiments, the absorbent material and/or the wound contact layer comprises carboxymethylated cellulose fibers. In certain embodiments, the wound contact layer comprises reinforcing nylon stitching. In certain embodiments the wound dressing further comprises fenestrations in the one or more of the plurality of layers of absorbent material.

In certain embodiments, the system further comprises an absorbent indicator and an adhesive member, wherein the adhesive member adheres the flexible connector and the absorbent indicator to the wound dressing. In certain embodiments, the absorbent indicator is positioned in a flow pathway at a location between the absorbent layer and the flexible connector; and the absorbent indicator is capable of absorbing exudate to indicate the presence of exudate at the side of the absorbent layer furthest from the wound. In certain embodiments, the wound exudate management system further comprises a status indicator, wherein the status indicator provides visual cues indicating when the pump is off, on, and/or on but malfunctioning.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Although the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected.

Certain embodiments of the present application relate to a wound dressing for use in a negative pressure wound therapy system, the wound dressing comprising: an adhesive layer for adhering the wound dressing adjacent to a wound; a wound contact layer for contacting the wound; a backing layer comprising a port; a tube having a first end connected with the port and an opposite second end; a first fitting connected to the second end of the tube, the first fitting configured for connection with a second fitting of the negative pressure wound therapy system to apply a negative pressure via the port; and a filter disposed within the first fitting, wherein the filter is formed of a hydrophilic material and has an average pore size of at least 2 microns; wherein the wound dressing is sterilized.

In certain embodiments, the average pore size is about 3 microns. In certain embodiments, the hydrophobic material comprises polyethersulfone (PESU). In certain embodiments, the wound dressing is sterilized by ethylene oxide (EO) sterilization. In certain embodiments, the wound dressing further comprises a check valve seated in the first fitting. In certain embodiments, the wound dressing further comprises a pressure dispersion layer; wherein the backing layer is adjacent to and in contact with the adhesive layer and the pressure dispersion layer. In certain embodiments, the wound dressing further comprises a plurality of layers of absorbent material disposed between the wound contact layer and the pressure dispersion layer, wherein the plurality of layers of absorbent material includes a first absorbent material layer facing the wound contact layer and a second absorbent material layer facing the pressure dispersion layer. In certain embodiments, the wound dressing further comprises an absorbent indicator aligned with the port, the absorbent indicator configured to absorb exudate to indicate the presence of exudate in the second absorbent material layer.

Certain embodiments of the present application relate to a fitting configured for use with a wound dressing, the fitting comprising: a first end portion configured for coupling with a tube; a second end portion configured for coupling with a mating fitting; and a filter disposed in a chamber defined between the first end portion and the second end portion, wherein the filter is formed of a hydrophilic material and has an average pore size of at least 2 microns; wherein the fitting is sterilized.

In certain embodiments, the average pore size is about 3 microns. In certain embodiments, the hydrophobic material comprises polyethersulfone (PESU). In certain embodiments, the fitting further comprises a check valve seated in the chamber. In certain embodiments, the fitting is sterilized by ethylene oxide sterilization.

Certain embodiments of the present application relate to an apparatus comprising the fitting, the apparatus further comprising: a wound dressing for adhering about a wound; and a tube connecting the wound dressing with the fitting.

Certain embodiments of the present application relate to a system comprising the apparatus, the system further comprising: the mating fitting, wherein the fitting is engaged with the mating fitting; a second tube connected with the mating fitting; and a pump connected with the second tube such that the pump is operable to supply the wound dressing with a negative pressure.

Certain embodiments of the present application relate to a wound dressing for use in a negative pressure wound therapy system, the wound dressing comprising: an adhesive layer for adhering the wound dressing adjacent to a wound; a wound contact layer for contacting the wound; a backing layer comprising a port; a tube having a first end connected with the port and an opposite second end; a first fitting connected to the second end of the tube, the first fitting configured for connection with a second fitting of the negative pressure wound therapy system to apply a negative pressure via the port; and a filter disposed within the first fitting, wherein the filter is formed of polyethersulfone (PESU) and has an average pore size of at least 2 microns.

In certain embodiments, the average pore size is about 3 microns. In certain embodiments, the wound dressing is sterile. In certain embodiments, the wound dressing is sterilized by ethylene oxide (EO) sterilization. In certain embodiments, the wound dressing further comprises a check valve seated in the first fitting.

In certain embodiments, the wound dressing further comprises a pressure dispersion layer; wherein the backing layer is adjacent to and in contact with the adhesive layer and the pressure dispersion layer. In certain embodiments, the wound dressing further comprises a plurality of layers of absorbent material disposed between the wound contact layer and the pressure dispersion layer, wherein the plurality of layers of absorbent material includes a first absorbent material layer facing the wound contact layer and a second absorbent material layer facing the pressure dispersion layer. In certain embodiments, the wound dressing further comprises an absorbent indicator aligned with the port, the absorbent indicator configured to absorb exudate to indicate the presence of exudate in the second absorbent material layer.

Certain embodiments of the present application relate to a fitting configured for use with a wound dressing, the fitting comprising: a first end portion configured for coupling with a tube; a second end portion configured for coupling with a mating fitting; and a filter disposed in a chamber defined between the first end portion and the second end portion, wherein the filter is formed of polyethersulfone (PESU) and has an average pore size of at least 2 microns; wherein the fitting is sterilized by ethylene oxide sterilization.

In certain embodiments, the average pore size is about 3 microns. In certain embodiments, the fitting further comprises a check valve seated in the chamber.

Certain embodiments of the present application relate to an apparatus comprising the fitting, and further comprising: a wound dressing for adhering about a wound; and a tube connecting the wound dressing with the fitting.

Certain embodiments of the present application relate to a a system comprising the apparatus, and further comprising: the mating fitting, wherein the fitting is engaged with the mating fitting; a second tube connected with the mating fitting; and a pump connected with the second tube such that the pump is operable to supply the wound dressing with a negative pressure.

Certain embodiments of the present application relate to a negative pressure wound therapy system, comprising: a wound dressing for adhering adjacent to a wound; tubing connected to the wound dressing; a pump connected with the tubing and configured to supply a negative pressure to the wound dressing via the tubing; and an inline filter disposed within the tubing, wherein the filter is formed of polyethersulfone (PESU), has an average pore size of at least 2 microns, and is configured to discourage passage of exudate from the wound dressing to the pump.

In certain embodiments, the average pore size is about 3 microns. In certain embodiments, the tubing comprises: a first tube having a first tube first end and an opposite first tube second end, wherein the first tube first end is connected with the wound dressing, and wherein the first tube second end comprises a first fitting; and a second tube having a second tube first end and an opposite second tube second end, wherein the second tube first end comprises a second fitting mated with the first fitting, and wherein the second tube second end is in fluid communication with the pump; wherein the inline filter is disposed within one of the first fitting or the second fitting. In certain embodiments, the inline filter is disposed within the first fitting. In certain embodiments, the first fitting further comprises a check valve configured to permit fluid flow through the first fitting away from the wound dressing and to prevent fluid flow through the first fitting toward the wound dressing. In certain embodiments, the wound dressing and the inline filter are sterilized by ethylene oxide sterilization. In certain embodiments, the wound dressing further comprises an absorbent indicator configured to absorb exudate to indicate the presence of exudate in the wound dressing.

It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A wound dressing for use in a negative pressure wound therapy system, the wound dressing comprising:
   an adhesive layer for adhering the wound dressing adjacent to a wound;
   a wound contact layer for contacting the wound;
   a backing layer comprising a port;
   a tube having a first end connected with the port and an opposite second end;
   a first fitting connected to the second end of the tube, the first fitting configured for connection with a second fitting of the negative pressure wound therapy system to apply a negative pressure via the port; and
   a filter assembly including the first fitting,
   wherein:
   the filter assembly includes a filter membrane that is formed of polyethersulfone (PESU) and has an average pore size of between 2 to 5 microns;
   the filter assembly includes an inlet, an outlet, and a cartridge arranged between the inlet and the outlet in an axial direction;
   the cartridge includes a cavity, a check valve at least partially arranged in the cavity, and the filter membrane arranged at least partially in the cavity adjacent to the check valve;
   the cavity is formed in a housing of the filter assembly and the inlet is formed in the housing such that an inlet opening of the inlet extends through the housing to the cavity;
   the filter membrane and the check valve are arranged in the cavity such that the filter membrane and the check valve are at least partially surrounded by the housing in the axial direction;
   the inlet opening has a constant diameter in the axial direction;
   the inlet opening having the constant diameter in the axial direction opens into the cavity at a cavity inlet of the cavity; and
   the filter membrane is located at, and aligned in the axial direction with, the cavity inlet of the cavity.

2. The wound dressing of claim 1, wherein the average pore size is about 3 microns.

3. The wound dressing of claim 1, wherein the wound dressing is sterile.

4. The wound dressing of claim 3, wherein the wound dressing is sterilized by ethylene oxide (EO) sterilization.

5. The wound dressing of claim 1, further comprising a pressure dispersion layer;
   wherein the backing layer is adjacent to and in contact with the adhesive layer and the pressure dispersion layer.

6. The wound dressing of claim 5, further comprising:
   a plurality of layers of absorbent material disposed between the wound contact layer and the pressure dispersion layer, wherein the plurality of layers of absorbent material includes a first absorbent material layer facing the wound contact layer and a second absorbent material layer facing the pressure dispersion layer.

7. The wound dressing of claim 6, further comprising an absorbent indicator aligned with the port, wherein the absorbent indicator is configured to absorb exudate to indicate the presence of exudate in the second absorbent material layer.

8. The wound dressing of claim 1, wherein:
   the cavity inlet is at least partially defined by a planar interior surface of the housing; and
   the filter membrane is in direct contact with the planar interior surface.

9. A negative pressure wound therapy system, comprising:
   a wound dressing for adhering adjacent to a wound;
   tubing connected to the wound dressing;
   a pump connected with the tubing and configured to supply a negative pressure to the wound dressing via the tubing; and
   an inline filter assembly,
   wherein:
   the inline filter assembly includes at least one filter membrane that is formed of polyethersulfone (PESU), has an average pore size of between 2 to 5 microns, and is configured to discourage passage of exudate from the wound dressing to the pump;
   the inline filter assembly includes an inlet, an outlet, and a cartridge arranged between the inlet and the outlet in an axial direction;
   the cartridge includes a cavity, a check valve at least partially arranged in the cavity, and the at least one filter membrane arranged at least partially in the cavity adjacent to the check valve;
   the check valve and the at least one filter membrane are aligned in the cavity along a central axis extending from the inlet to the outlet;
   the cavity is formed in a housing of the inline filter assembly and the inlet is formed in the housing such that an inlet opening of the inlet extends through the housing to the cavity;
   the at least one filter membrane and the check valve are arranged in the cavity such that the at least one filter membrane and the check valve are at least partially surrounded by the housing in the axial direction;
   the inlet opening has a constant diameter in the axial direction;
   the inlet opening having the constant diameter in the axial direction opens into the cavity at a cavity inlet of the cavity; and
   the at least one filter membrane is located at, and aligned in the axial direction with, the cavity inlet of the cavity.

10. The negative pressure wound therapy system of claim 9, wherein the average pore size is about 3 microns.

11. The negative pressure wound therapy system of claim 9, wherein the tubing comprises:
    a first tube having a first tube first end and an opposite first tube second end, wherein the first tube first end is connected with the wound dressing, and wherein the first tube second end comprises a first fitting; and
    a second tube having a second tube first end and an opposite second tube second end, wherein the second tube first end comprises a second fitting connected to the first fitting by the inline filter assembly, and wherein the second tube second end is in fluid communication with the pump;

wherein the inline filter assembly is adapted to be disposed at least partially in one of the first fitting or the second fitting.

12. The negative pressure wound therapy system of claim 11, wherein the inline filter assembly is adapted to be disposed at least partially in the first fitting.

13. The negative pressure wound therapy system of claim 9, wherein the wound dressing and the inline filter assembly are sterilized by ethylene oxide sterilization.

14. The negative pressure wound therapy system of claim 9, wherein the wound dressing further comprises an absorbent indicator configured to absorb exudate to indicate the presence of exudate in the wound dressing.

15. The negative pressure wound therapy system of claim 9, wherein:
   the cavity inlet is at least partially defined by a planar interior surface of the housing; and
   the filter membrane is in direct contact with the planar interior surface.

* * * * *